United States Patent [19]
Cutright et al.

[11] Patent Number: 5,631,429
[45] Date of Patent: May 20, 1997

[54] METHOD AND APPARATUS RELATING TO TEST EQUIPMENT WITH HUMIDIFICATION CAPABILITY

[75] Inventors: Robert A. Cutright, Holland; Richard Walker, Hudsonville; Wayne Walton, Holland, all of Mich.

[73] Assignee: Venturedyne, Ltd., Milwaukee, Wis.

[21] Appl. No.: 550,463

[22] Filed: Oct. 30, 1995

[51] Int. Cl.⁶ .................................................. G01N 17/00
[52] U.S. Cl. ........................................................ 73/865.6
[58] Field of Search ................................. 73/865.6, 760, 73/763; 324/760

[56] References Cited

U.S. PATENT DOCUMENTS

| | | | |
|---|---|---|---|
| 3,424,231 | 1/1969 | Truhan | 165/19 |
| 3,464,400 | 9/1969 | Wellman | 126/113 |
| 3,464,401 | 9/1969 | McGrath | 126/113 |
| 3,478,817 | 11/1969 | Shaw | 165/21 |
| 3,756,311 | 9/1973 | Bitz | 165/21 |
| 3,870,873 | 3/1975 | Mallory | 240/1.1 |
| 4,004,432 | 1/1977 | Kong et al. | 62/262 |
| 4,483,197 | 11/1984 | Kellner | 73/865.6 |
| 4,812,750 | 3/1989 | Keel et al. | 73/865.6 |
| 4,825,847 | 5/1989 | Perron | 126/113 |
| 4,854,726 | 8/1989 | Lesley et al. | 73/865.6 |
| 5,043,143 | 8/1991 | Shaw et al. | 422/65 |
| 5,072,177 | 12/1991 | Liken et al. | 324/158 F |
| 5,188,169 | 2/1993 | Lim | 165/20 |
| 5,191,282 | 3/1993 | Liken et al. | 324/158 F |
| 5,195,384 | 3/1993 | Duesler, Jr. et al. | 73/865.6 |
| 5,220,956 | 6/1993 | Noble, Jr. et al. | 165/80.2 |
| 5,259,553 | 11/1993 | Shyu | 236/49.3 |
| 5,268,637 | 12/1993 | Liken et al. | 324/158 F |
| 5,301,744 | 4/1994 | Derks | 165/16 |
| 5,305,822 | 4/1994 | Kogetsu et al. | 165/12 |
| 5,318,361 | 6/1994 | Chase et al. | 73/865.6 |
| 5,346,128 | 9/1994 | Wacker | 236/44 A |
| 5,346,129 | 9/1994 | Shah et al. | 236/44 |

*Primary Examiner*—Richard Chilcot
*Assistant Examiner*—Max H. Noori
*Attorney, Agent, or Firm*—Jansson & Shupe, Ltd.

[57] ABSTRACT

A new method provides test equipment having a humidification capability. Such method includes the steps of fabricating equipment having (a) a chamber for stress-testing products placed therein, and (b) a cavity for receiving a module. The equipment is installed in a product test facility and used for stress-testing (by, e.g., "temperature cycling") a first group of products placed in the chamber. Later (perhaps several months or years later), the module is mounted in the cavity, a second group of products is placed in the chamber and humidity-controlled air is circulated across the second group of products. The new method is particularly useful for manufacturers or testers of products like electronic printed circuit boards initially requiring only a temperature-related testing capability but later needing to add humidity-related testing regimens.

16 Claims, 4 Drawing Sheets

METHOD AND APPARATUS RELATING TO TEST EQUIPMENT WITH HUMIDIFICATION CAPABILITY

FIELD OF THE INVENTION

This invention relates generally to heat exchange equipment and, more particularly, to such equipment with a humidification capability.

BACKGROUND OF THE INVENTION

Most types of electronic gear, e.g., TV sets, aircraft navigation systems, radio transceivers and the like, incorporate circuit boards made of thin, flat dielectric sheet. Such sheet has resistors, capacitors, integrated circuits and other components mounted on it. While some boards are "hard wired" using conventional soldered wire, printed circuit boards (or "PC boards") are more common. PC boards employ flat foil strips (applied by a process akin to printing) as the "wiring" for component interconnection.

Many applications for PC boards involve hostile operating environments particularly including temperature extremes and, sometimes, rapid excursions between such extremes. And the operating environment may also include vibration which must be withstood by the PC boards. Unless recognized in board construction and testing, such environments can cause premature failure of the board per se and/or of the components mounted thereon.

To help assure that PC boards provide the requisite degree of reliability in such applications, board manufacturers often subject them to temperature tests (often referred to as "stress tests" or "stress screening") by placing them in an environmental chamber capable of producing rapid and extreme changes in temperature. For example, such a chamber might provide a temperature change of from −40° F. to over 200° F. in about 30 minutes. The stress test may also include vibrating the PC boards being subjected to such temperature extremes.

Stress screening culls out PC boards that exhibit what is often called "infant mortality," i.e. boards which fail prematurely under the rigors of such screening. A prominent designer and manufacturer of such environmental test chambers is Thermotron Industries of Holland, Mich.

More recently, those who make PC boards have sometimes been required to impose yet an additional form of stress—that of changing humidity. An example of an application for PC boards subjected to the additional rigors of humidity testing is aircraft electronic systems. Both commercial and military aircraft can be exposed to both very dry ambient air and very humid ambient air in a relatively short time if the aircraft moves between, say, a desert site and a jungle-like site.

Until the advent of the invention, those who test PC boards by stress screening them had three choices, none of them particularly attractive from an economic standpoint. One choice was to anticipate the need for humidity testing by purchasing (at added cost) an environmental test chamber configured with a humidity-changing capability. But relatively few PC boards are required to be tested under controlled humidity conditions—the humidity-related components may be underutilized or not used at all.

Another choice was to buy an environmental test chamber which was devoid of humidity-changing components and hope that its testing business could be sustained without having to offer that capability. And if the need to provide humidity-based testing arose, the existing chamber would be rebuilt (at substantial expense) to add a humidity control feature. If the chamber used welded seams, some of those seams had to be opened and are not easy to re-close. If not properly sealed, water gets into the fiberglass insulation behind the sheet metal—and wet fiberglass is a poor heat insulator.

A third choice is to simply purchase another chamber having a humidity control feature. In that dismaying event, one or both chambers may be grossly under-utilized and the capital investment is very substantial.

A method and apparatus overcoming some of the problems and shortcomings of the prior art would be an important advance.

OBJECTS OF THE INVENTION

It is an object of the invention to provide a method and apparatus overcoming some of the problems and shortcomings of the prior art.

Another object of the invention is to provide a method and apparatus relating to environmental chambers used for "stress-testing" electrical products.

Another object of the invention is to provide a method and apparatus relating to test chambers having a humidification capability.

Yet another object of the invention is to provide a method and apparatus which reduce investment in capital equipment.

Another object of the invention is to provide a method and apparatus which avail the user of an opportunity to apply test regimens involving humidity-based testing.

Still another object of the invention is to provide a method and apparatus involving quick, easy addition of a humidification capability to a test chamber.

Another object of the invention is to provide a method and apparatus which obviates the need to acquire largely-duplicative test equipment.

Another object of the invention is to provide a method and apparatus which obviates the need to open welded seams in existing test chambers to add a humidification capability. How these and other objects are accomplished will become apparent from the following descriptions and from the drawings.

SUMMARY OF THE INVENTION

The inventive method involves testing electrical products using temperature-based regimens and, later, using regimens that involve circulating humidity-controlled air around the products. Such method includes the steps of fabricating test equipment having (a) a chamber for stress-testing products placed therein, and (b) a cavity for receiving a humidity module. The equipment is installed in a product test facility and used for stress-testing (by, e.g., "temperature cycling") a first group of products placed in the chamber. Later (perhaps several months or years later), a humidity module is mounted in the cavity, a second group of products is placed in the chamber and humidity-controlled air is circulated across the second group of products.

In a more specific aspect of the invention, the fabricating step includes providing a water vapor conduit in the equipment. Preferably, such conduit is in flow communication between the cavity and the chamber. Until the humidity module is added, the conduit is connected only to a drain tube to remove any condensate forming in the chamber. And for easier module mounting, fabricating the equipment also includes providing a plurality of electrical connections, terminal blocks or the like, in the cavity.

When the equipment user later needs to acquire the capability of testing with humidity-related regimens, the humidity module is manufactured, preferably to include a water reservoir and a steam generator to be, by either factory or field connection, in water-flow communication with the reservoir. Preferred module manufacturing also includes providing a connection to the water reservoir for attachment of a source of water. Such water source may be a pipe connected to a factory water supply if such pipe is readily available. If not, the source of water is a re-fillable water storage tank that forms a part of the module or that may be field-mounted as a part of such module.

When the module is mounted to permit humidity-related product testing, electrical wiring is extended between the module and the electrical connections. And during module mounting, the water vapor conduit is connected between the module and the chamber. Thereafter, the equipment user may stress-test products under humidity-controlled conditions by repetitively changing the temperature of the humidity-controlled air circulating across such products.

The improved test equipment has a chamber for stress-testing products placed in the chamber and also has a vacant cavity in the equipment for receiving a humidity module. The equipment may thereby be later configured to circulate humidity-controlled air across products placed in the chamber.

The highly-preferred equipment has a conduit extending between the cavity and the chamber. Such conduit has a terminus, e.g., a stub end or the like that is accessible from the cavity. Condensate can flow out of the chamber and when a humidity module is later installed, it may thereby be conveniently connected to the conduit so that water vapor can be introduced into the chamber.

The new method and equipment are particularly useful for manufacturers or testers of products like electronic printed circuit boards. Such manufacturer and testers may initially require only a temperature-related testing capability—the new equipment sans humidity module provides that capability at very little cost over standard equipment lacking such capability. Later, the humidity module may be added without the necessity of substantial disassembly of the equipment.

DETAILED DESCRIPTION OF PREFERRED EMBODIMENTS

The inventive method involves testing electrical products using temperature-based regimens. Later (and after installing a humidity module), other products are tested using regimens that involve circulating humidity-controlled air around such products.

Figure 1:
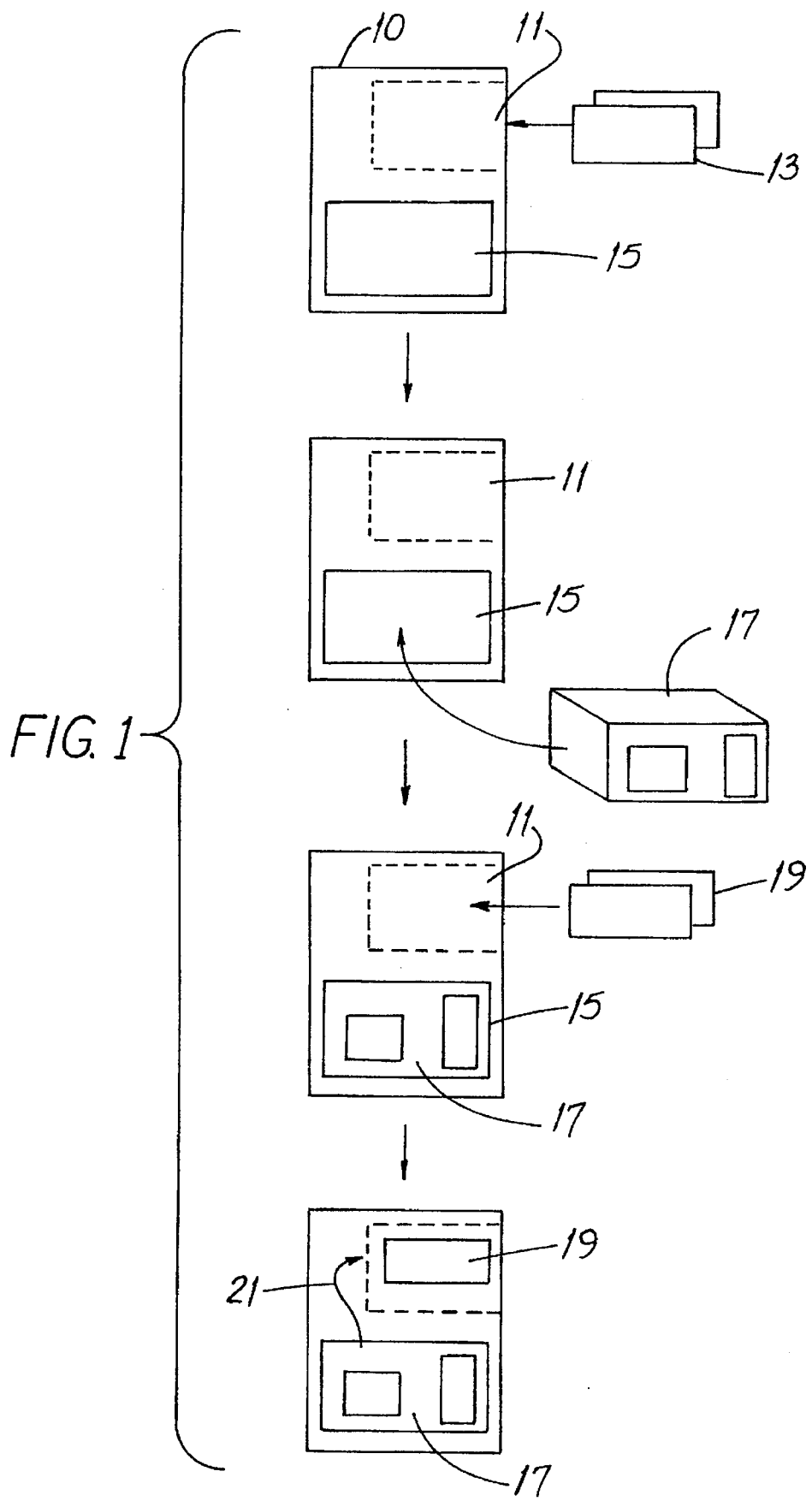
FIG. 1 is a representative diagram showing steps of the new method.

Referring first to FIG. 1, the broad method includes the steps of fabricating test equipment 10 having (a) a chamber 11 for stress-testing a first group of products 13 placed therein. Merely as an example, such products 13 may include printed circuit (PC) boards, with or without ancillary hardware. The equipment 10 has a vacant cavity 15 for later receiving a humidity module 17, details of which are described below.

The equipment 10 is installed in a factory or other type of product test facility and used for stress-testing (by, e.g., "temperature cycling") the first group of products 13 placed in the chamber 11. Later (perhaps several months or years later), a humidity module 17 is mounted in the cavity 15, a second group of products 19 is placed in the chamber 11 and humidity-controlled air (represented by the arrow 21) is circulated across the second group of products.

Figure 3:
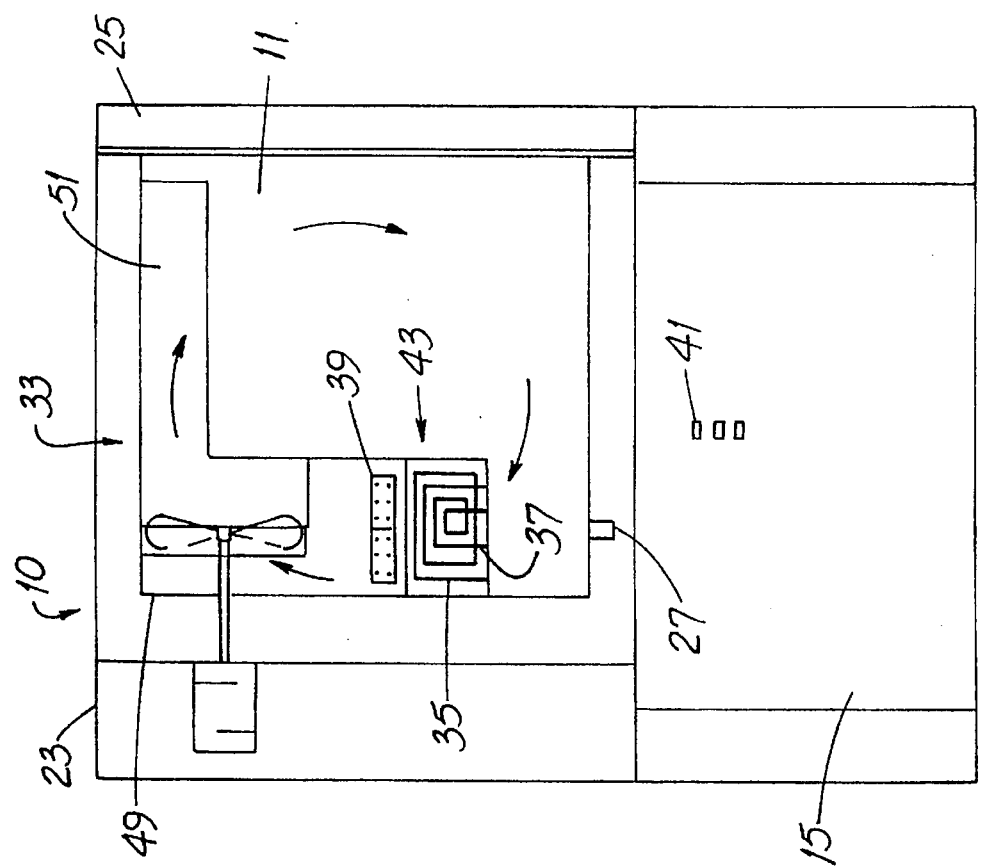
FIG. 3 is a side elevation view of the test equipment of FIG. 2. Parts are omitted.
Figure 2:
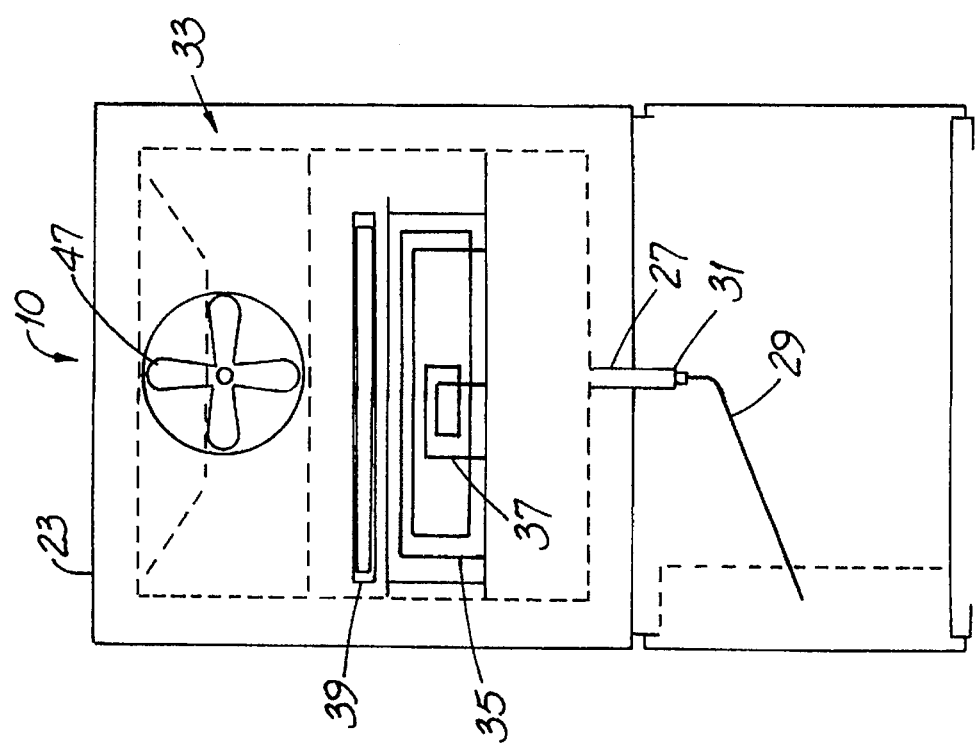
FIG. 2 is a front elevation view showing test equipment suitable for product testing using only temperature-based regimens and including features permitting later conversion to equipment also useful to test products using humidity-controlled air. Parts are omitted and surfaces of parts are shown in dashed outline.

Referring next to FIGS. 2 and 3, the test equipment 10 used to carry out temperature-based testing regimens (and capable of only being so used) has an enclosure 23 and a chamber 11 into which products to be tested are placed. A door 25 is used to close such chamber 11.

Products such as groups of products 13 or 19 may be placed into such chamber 11 using arrangements such as those shown in U.S. Pat. No. 5,072,177 (Liken et al.); U.S. Pat. No. 5,191,282 (Liken et al.) and U.S. Pat. No. 5,268,637 (Liken et al.), all of which are commonly owned with this application. And a typical temperature-based regimen may change the temperature of the products from, say, −20° F. to over 150° F. in about 30 minutes.

During initial fabrication of the test equipment 10, a water vapor conduit 27 is provided to be in flow communication between the cavity 15 and the chamber 11. The conduit 27 is attached to a drain tube 29 and until a humidity module 17 is later added, such conduit 27 is only used to drain condensate from within the chamber 11. The conduit 27 has a terminus 31, e.g., a stub end or the like that is accessible from the cavity 15. When a humidity module 17 is later installed, it may thereby be conveniently connected to the conduit 27. (After analyzing this specification, persons of ordinary skill will recognize that the conduit 27 mounted during initial fabrication may be replaced with another conduit having a separate connection point for a steam line mounted at the time of module installation.)

The equipment 10 is initially fabricated to also include an air duct 33 having a cooling coil 35 (the evaporator coil of a refrigeration system), a dehumidifying coil 37 and at least one heater 39 therein. It is to be appreciated that the de-humidifying coil 37 is inactive, i.e., not used for product testing based only upon changes in temperature. For easier module mounting, fabricating the equipment 10 also includes providing a plurality of electrical connections 41, terminal blocks or the like, in the cavity 15.

In the specific embodiment shown in FIG. 3, the air duct 33 is, in side view, shaped like an inverted L and the cooling coil 35, de-humidifying coil 37 and heaters 39 are in the first or inlet portion 43 of the duct 33 with the heaters 39 being in downstream air flow relationship to the coils 35, 37. A circulating fan 47 is at the junction 49 of the inlet portion 43 and the second or outlet portion 51. Air is drawn into the duct 33 near the bottom of the inlet portion 43, flows across the coils 35, 37 and heaters 39 and then flows from the outlet portion 51 into the chamber 11 and thence to the inlet portion 43.

Figure 4:
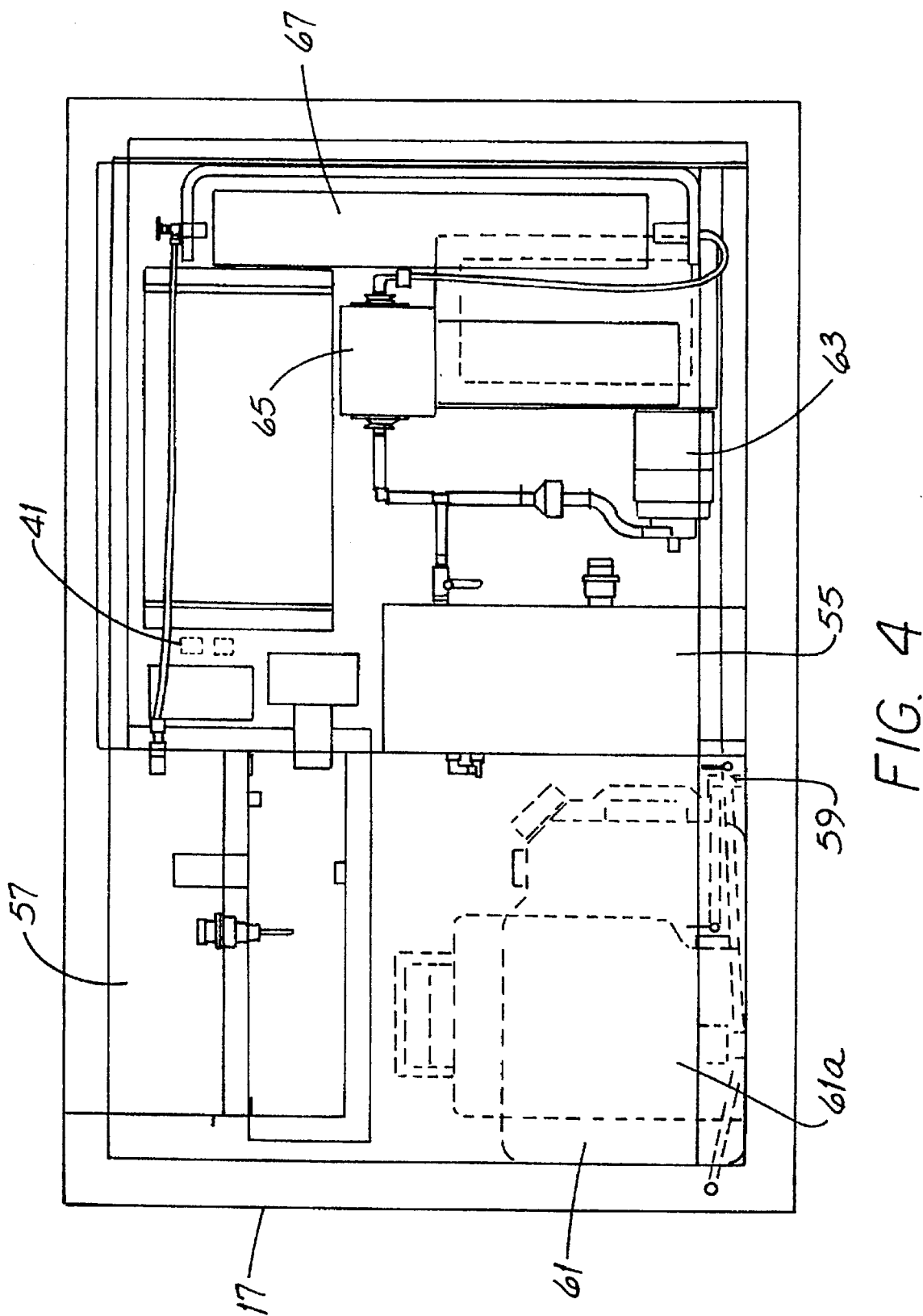
FIG. 4 is an elevation view of a humidity module useful with the test equipment of FIGS. 2 and 3. Parts are shown in dashed outline.
Figure 6:
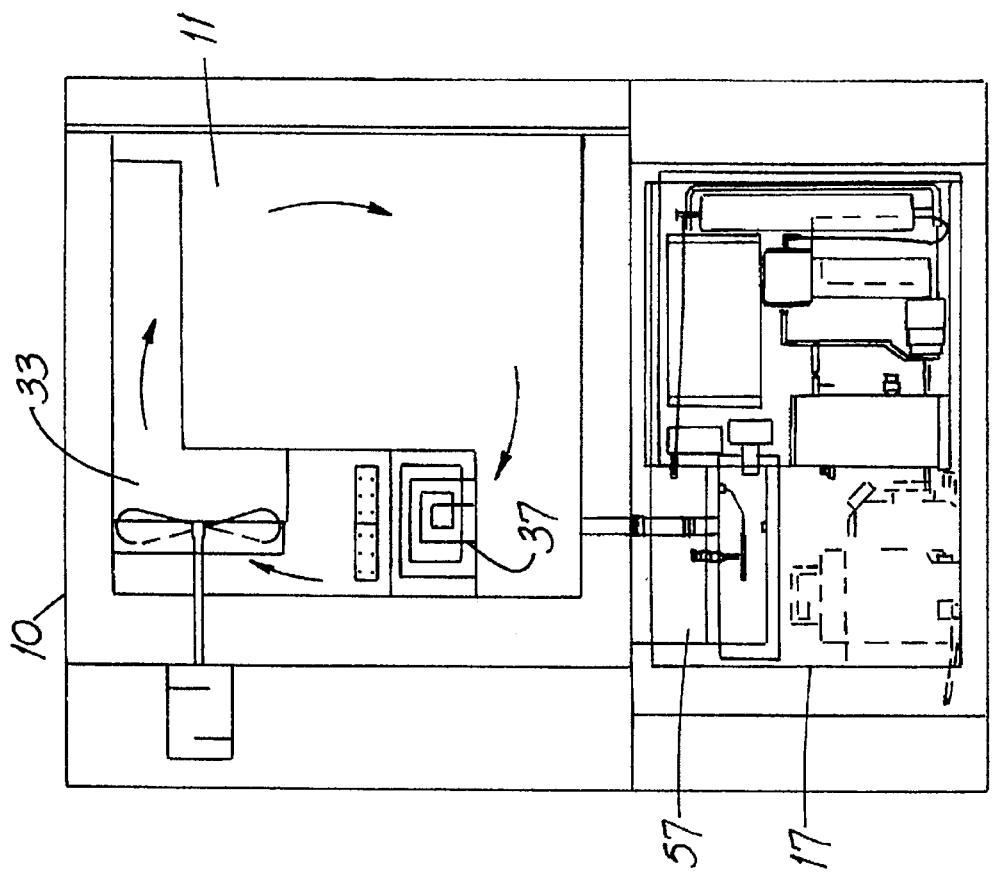
FIG. 6 is a side elevation view of the test equipment of FIG. 5. Parts are omitted.
Figure 5:
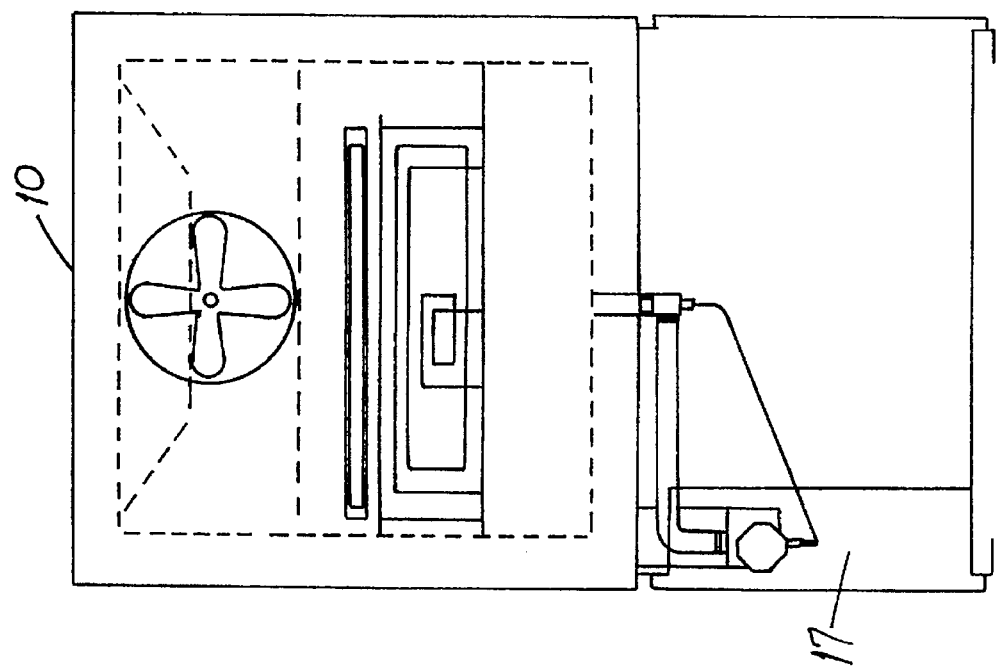
FIG. 5 is a front elevation view showing test equipment including the module of FIG. 4 and suitable for product testing using temperature-based regimens, humidity-controlled air or both. Parts are omitted and surfaces of parts are shown in dashed outline.

Referring next to FIGS. 4, 5 and 6 when the equipment user later needs to acquire the capability of testing with humidity-related regimens, the humidity module 17 is manufactured and includes a water reservoir 55 and a steam generator 57 to be, by either factory or field connection, in water-flow communication with the reservoir 55. Preferred module manufacturing also includes providing a connection 59 to the water reservoir 55 for attachment of a source of water 61. Such water source 61 may be a pipe connected to a factory water supply if such water supply is readily available. If not, the source of water 61 is a re-fillable water storage tank 61a that forms a part of the module 17 or that may be field-mounted as a part of such module 17.

When the module 17 is mounted to permit humidity-related product testing, electrical wiring is extended between the module 17 and the electrical connections 41. During module mounting, the water vapor conduit 27 (also referred to herein as a steam line) is connected between the module 17 and the chamber 11 and, specifically, between the module steam generator 57 and the air duct 33. A preferred module 17 also includes a water pump 63, a water filter 65 and a demineralizing tank 67 for conditioning water directed to the steam generator 57. After mounting and connecting the module 17, the equipment user may stress-test products under humidity-controlled conditions by repetitively changing the relative humidity of air circulating across the products or by changing both the temperature and the humidity of such air.

As used herein, the phrase "temperature-based," as applied to a testing regimen, means a regimen that tests solely by using controlled temperature extremes. The phrase "humidity-controlled air" means air, the relative humidity of which is controllably varied for product testing purposes.

While the principles of the invention have been shown and described in connection with specific embodiments, it is to be understood clearly that such embodiments are by way of example and are not limiting.

What is claimed:

1. A method for testing electrical products and including the steps of:

fabricating test equipment having an enclosure containing (a) a chamber for stress-testing products placed therein, (b) a vacant cavity for receiving a humidity module, and (c) a water vapor conduit in flow communication with the chamber;

installing the equipment in a product test facility;

stress-testing a first group of products placed in the chamber by changing the temperature of air around the products;

mounting the module in the cavity;

placing a second group of products in the chamber; and circulating humidity-controlled air across the second group of products.

2. The method of claim 1 wherein the fabricating step includes providing an air duct within the enclosure for directing air along a path above the chamber and downwardly into the chamber, the duct having a de-humidifying coil therein which is maintained inactive during the stress-testing step.

3. The method of claim 2 wherein the fabricating step also includes providing an evaporator coil therein for use when testing products using only temperature-based regimens.

4. The method of claim 1 wherein the circulating step includes repetitively changing the temperature of the humidity-controlled air circulating across the second group of products.

5. The method of claim 1 wherein the water vapor conduit is in flow communication between the cavity and the chamber.

6. The method of claim 1 wherein the fabricating step includes providing a plurality of electrical connections in the cavity.

7. The method of claim 6 wherein the mounting step includes extending electrical wiring between the module and the electrical connections.

8. The method of claim 1 wherein the mounting step includes connecting the water vapor conduit between the module and the chamber.

9. The method of claim 1 wherein the mounting step is preceded by the step of:

manufacturing the humidity module to include a water reservoir to be in water-flow communication with the reservoir.

10. The method of claim 9 wherein the manufacturing step includes providing a connection to the water reservoir for attachment of a source of water.

11. The method of claim 10 wherein the source of water is a pipe connected to a factory water supply.

12. The method of claim 10 wherein the source of water is a re-fillable water storage tank.

13. In equipment for testing electronic products and having an enclosure containing a chamber for stress-testing circuit boards placed therein, the improvement comprising:

a vacant cavity within the enclosure for receiving a humidity module, thereby configuring the equipment to later receive the humidity module, thereupon enabling the equipment to circulate humidity-controlled air across products placed in the chamber.

14. The equipment of claim 13 including a water vapor conduit extending between the cavity and the chamber.

15. The equipment of claim 14 wherein the conduit includes a closure preventing air from flowing between the cavity and the chamber.

16. The equipment of claim 14 wherein the conduit includes a terminus accessible from the cavity, thereby configuring the equipment for convenient connection of the humidity module to the conduit.

* * * * *